United States Patent [19]

Zaicow et al.

[11] Patent Number: 5,340,538
[45] Date of Patent: Aug. 23, 1994

[54] STERILIZING GAS DELIVERY METHOD

[75] Inventors: Todd A. Zaicow, Griffith, Ind.; Scott A. Farber; Daniel F. Bartel, both of Chicago, Ill.

[73] Assignee: Liquid Carbonic Corporation, Oak Brook, Ill.

[21] Appl. No.: 127,434

[22] Filed: Sep. 27, 1993

[51] Int. Cl.$^5$ .................................. A61L 2/16
[52] U.S. Cl. .......................... 422/33; 222/3; 422/34; 422/40
[58] Field of Search ............ 422/33, 34, 40, 305; 222/1, 3

[56] References Cited

U.S. PATENT DOCUMENTS

| | | | |
|---|---|---|---|
| 2,007,738 | 7/1935 | Baer | 422/34 X |
| 2,891,838 | 6/1959 | Kaye . | |
| 2,899,266 | 3/1957 | Gewalt et al. | 21/58 |
| 2,965,936 | 12/1960 | Kaye | 422/34 X |
| 3,054,270 | 9/1962 | Huston | 422/34 X |
| 3,238,096 | 3/1966 | Kaye . | |
| 3,436,173 | 4/1969 | Power | 422/34 X |
| 3,473,886 | 10/1969 | Leeds | 422/34 X |
| 3,476,507 | 11/1969 | Leeds | 222/3 X |
| 3,489,505 | 8/1967 | Schumann et al. | 21/91 |
| 3,498,742 | 3/1970 | Long | 422/34 X |
| 4,130,393 | 12/1978 | Fox | 422/31 |
| 4,954,284 | 9/1990 | Batt et al. | 252/170 |
| 5,128,101 | 7/1992 | Boynton | 422/31 |

Primary Examiner—Robert J. Warden
Assistant Examiner—Krisanne M. Thornton
Attorney, Agent, or Firm—Fitch, Even, Tabin & Flannery

[57] ABSTRACT

The present invention is directed to a method for dispensing a sterilizing gas. In the method, a liquid mixture of ethylene oxide and carbon dioxide is provided. A cylinder is partially filled with the liquid mixture of ethylene oxide and carbon dioxide. The head space of the cylinder is then pressurized with an inert gas at a pressure substantially higher than the vapor pressure of the liquid mixture of ethylene oxide and carbon dioxide. The liquid gas mixture is then dispensed from the cylinder under conditions whereby the head space pressure is maintained greater than the vapor pressure of the liquid mixture of ethylene oxide and carbon dioxide.

7 Claims, No Drawings

STERILIZING GAS DELIVERY METHOD

FIELD OF THE INVENTION

The present invention is directed to a delivery system for dispensing a sterilizing gas. More particularly, the present invention is directed to the use of a sterilizing gas consisting of ethylene oxide and carbon dioxide and to a method for dispensing the sterilizing gas mixture.

BACKGROUND OF THE INVENTION

It is well known to use ethylene oxide as a sterilizing gas. Ethylene oxide in pure form, however, is highly poisonous and can be explosive. Consequently, ethylene oxide is commercially delivered as a mixture having a low level of ethylene oxide distributed in an inert gas. U.S. Pat. No. 2,891,838 to Kaye, U.S. Pat. No. 3,238,096 to Kaye and U.S. Pat. No. 4,954,284 to Batt et al. describe such systems. The inert gas choice has been Freon 12, which is dichlorodifhoromethane. As is well known, the use of chlorofluoro compounds is being phased out of commercial use. It would be highly desirable to provide a commercial mixture of ethylene oxide in an inert gas which is not hazardous or harmful to the atmosphere. A highly desirable inert gas for use with ethylene oxide is carbon dioxide. However, in the liquid state ethylene oxide is only partially miscible with carbon dioxide. When placed in a pressurized cylinder, the carbon dioxide tends to occupy the head space of the cylinder as the mixture of gases is dispensed. Consequently, the ethylene oxide in the liquid phase becomes increasingly more concentrated as the gas undergoes dispensing. This complicates the use of the ethylene oxide as a sterilizing medium since the amount of gas to be used is uncertain because of the concentration gradient that occurs during the dispensing process. The problems of using carbon dioxide as a diluting gas are described in U.S. Pat. No. 5,128,101 to Boynton.

U.S. Pat. No. 2,007,738 to Baer early recognized the desirability of using ethylene oxide and carbon dioxide. The Baer patent recognized the problem of immiscibility of ethylene oxide and carbon dioxide. The solution to this problem was solved in the Baer patent by dispensing the entire contents of a liquid mixture of ethylene oxide and carbon dioxide to an accumulator which was at a lower pressure. The two gases vaporize and the gaseous mixture in the accumulator could be dispensed with a constant level of ethylene oxide in the mixture of gases.

U.S. Pat. No. 2,965,936 to Kaye also discloses a one-shot ethylene oxide and carbon dioxide mixture which was dispensed from an ampoule which provided small amounts of an ethylene oxide and carbon dioxide mixture.

It would be highly desirable to provide a means for dispensing desired amounts from a large source of ethylene oxide and carbon dioxide wherein the concentration of the ethylene oxide could be maintained relatively constant throughout the dispensing process.

Accordingly, it is a principal object of the present invention to provide a system for dispensing a liquid mixture of ethylene oxide and carbon dioxide, wherein the ethylene oxide level remains relatively constant throughout the dispensing process.

SUMMARY OF THE INVENTION

The present invention is directed to a method for dispensing a sterilizing gas. In the method, a liquid mixture of ethylene oxide and carbon dioxide is provided. A cylinder is partially filled with the liquid mixture of ethylene oxide and carbon dioxide. The head space of the cylinder is then pressurized with an inert gas at a pressure substantially higher than the vapor pressure of the liquid mixture of ethylene oxide and carbon dioxide. The liquid gas mixture is then dispensed from the cylinder under conditions whereby the head space pressure is maintained greater than the vapor pressure of the liquid mixture of ethylene oxide and carbon dioxide.

DETAILED DESCRIPTION OF THE INVENTION

The ethylene oxide and carbon dioxide mixtures are charged into the liquid cylinder at a pressure of from about 580 psig to about 935 psig and at a temperature in the range of from about 50° F. to about 90° F. The ethylene oxide is present in the liquid mixture of ethylene oxide and carbon dioxide at a level of from about 8% to about 12%. The liquid mixture of ethylene oxide and carbon dioxide is charged into the cylinder at a level sufficient to occupy from about 40% to about 75% of the volume of the cylinder. An eductor tube is mounted in the cylinder so as to dispense the liquid mixture of carbon dioxide and ethylene oxide from the bottom of the cylinder.

After the liquid mixture of carbon dioxide and ethylene oxide is charged into the cylinder, the head space of the cylinder is pressurized to a pressure of from about 1800 psig to about 2200 psig. The vapor pressure of the liquid mixture of ethylene oxide and carbon dioxide is about 750 psig. The inert gas is selected from the group consisting of helium, nitrogen and argon. Preferably, the inert gas is helium.

As the liquid mixture of ethylene oxide and carbon dioxide is removed from the cylinder during dispensing, the volume occupied by the inert gas increases and the pressure of the inert gas is reduced. The relationship of the volume of the head space, the initial pressure of the inert gas in the head space and the volume occupied by the initial charge of the liquid mixture of ethylene oxide and carbon dioxide is adjusted so that the head space pressure remains above the vapor pressure of the mixture of ethylene oxide and carbon dioxide.

The following example further illustrates various features of the invention, but is intended to in no way limit the scope of the invention as set forth in the appended claims.

EXAMPLE 1

A liquid mixture of 8.5% ethylene oxide and 91.5% carbon dioxide was provided at a pressure of 750 psig and a temperature of 70° F. The liquid mixture was charged into a cylinder having a total volume of 2600 cubic inches at a level sufficient to occupy 60% of the volume of the cylinder.

The head space of the cylinder was then pressurized with helium to a total pressure of 2000 psig. An eductor tube was disposed within the cylinder to transfer the contents of the liquid mixture from the bottom of the cylinder. The liquid mixture of ethylene oxide and carbon dioxide was dispensed through suitable piping to a sterilizing chamber where it was vaporized to effect a sterilization cycle. The concentration of the first charge of ethylene oxide and carbon dioxide dispensed to the sterilizing chamber contained 8.5% ethylene oxide. After a series of 15 sterilization cycles, the concentration of the ethylene oxide was 8.5% in the final sterilization cycle.

The head space pressure after the final sterilization cycle was 1000 psig and <5% of the initial charge of the liquid mixture of ethylene oxide and carbon dioxide remained in the cylinder. Since this head space pressure was only marginally higher than the vapor pressure of ethylene oxide and carbon dioxide, no further sterilization cycles were initiated and the cylinder was recharged and re-pressurized prior to further use.

What is claimed is:

1. A method for dispensing a sterilizing gas, comprising:
   (a) providing a liquid mixture of ethylene oxide and carbon dioxide;
   (b) partially filling a cylinder with said mixture;
   (c) pressurizing the head space of said cylinder with an inert gas; and
   (d) dispensing said mixture as a liquid from said container under conditions whereby the head space pressure is greater than the vapor pressure of said mixture.

2. A method in accordance with claim 1, wherein said liquid mixture fills from 40% to 75% of the volume of said cylinder.

3. A method in accordance with claim 1, wherein said head space is pressurized to a pressure of from about 1800 psig to about 2200 psig.

4. A method in accordance with claim 1, wherein said liquid mixture has from about 6% to about 12% of ethylene oxide and from about 88% to about 92% of carbon dioxide.

5. A method in accordance with claim 1, wherein the said liquid mixture is filled into said cylinder at a pressure of from about 580 psig to about 935 psig and a temperature of from about 50° F. and about 90° F.

6. A method in accordance with claim 1, wherein said inert gas is selected from the group consisting of helium and nitrogen.

7. A method in accordance with claim 6, wherein said inert gas is helium.

* * * * *